(12) United States Patent
Yamada (10) Patent No.: US 7,239,732 B1
(45) Date of Patent: Jul. 3, 2007

(54) METHOD AND UNIT FOR STORING A RADIATION IMAGE

(75) Inventor: Masahiko Yamada, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 09/539,409

(22) Filed: Mar. 30, 2000

(30) Foreign Application Priority Data

| Mar. 31, 1999 | (JP) | ................................. 11-092786 |
| Nov. 11, 1999 | (JP) | ................................. 11-321463 |

(51) Int. Cl.
*G06K 9/00* (2006.01)

(52) U.S. Cl. ...................... 382/132; 128/922; 707/100
(58) Field of Classification Search ................ 382/100, 382/128, 130, 131, 132; 128/922
See application file for complete search history.

(56) References Cited

U.S. PATENT DOCUMENTS

| 4,258,264 A | | 3/1981 | Kotera et al. ............... 250/484 |
| 4,564,861 A | * | 1/1986 | Hishinuma et al. ......... 250/582 |
| 4,598,369 A | * | 7/1986 | Wang et al. .................. 378/22 |
| 4,751,507 A | * | 6/1988 | Hama et al. ................ 345/784 |
| 4,933,670 A | * | 6/1990 | Wislocki ..................... 345/167 |
| 4,944,189 A | * | 7/1990 | Nakajima et al. ......... 73/861.25 |
| 5,638,819 A | * | 6/1997 | Manwaring et al. ........ 600/424 |
| 5,889,894 A | | 3/1999 | Ito et al. ..................... 382/300 |
| 5,905,822 A | | 5/1999 | Ito et al. ..................... 382/300 |
| 6,445,943 B1 | * | 9/2002 | Ferre et al. ................. 600/424 |
| 6,470,207 B1 | * | 10/2002 | Simon et al. ............... 600/426 |
| 6,477,262 B2 | * | 11/2002 | Wang ......................... 382/132 |

FOREIGN PATENT DOCUMENTS

| JP | 56-11395 | 2/1981 |
| JP | 56-11397 | 2/1981 |
| JP | 405272952 A * | 10/1993 |

OTHER PUBLICATIONS

IBM Technical Disclosure Bulletin ("Selective Area Image Compression," vol. 29, Issue 12, p. No. 5356-5357, May 1, 1987).*

* cited by examiner

*Primary Examiner*—Vikkram Bali
*Assistant Examiner*—Anand Bhatnagar
(74) *Attorney, Agent, or Firm*—Sughrue Mion, PLLC (57) ABSTRACT

Radiation-image information is input from a radiation-image measuring apparatus to a measurement-information storing section, and measurement information, which consists of the positional information of a measuring point and a result of measurement based on the positional information, is also input from the radiation-image measuring apparatus to the measurement-information storing section. The measurement information is related to the radiation-image information by the measurement-information storing section and is stored in a storage medium.

29 Claims, 6 Drawing Sheets

METHOD AND UNIT FOR STORING A RADIATION IMAGE

BACKGROUND OF THE INVENTION

1. Field of the Invention

This invention relates generally to a method and unit for storing a radiation image, and more particularly to a method and unit for storing information on a measurement made on a radiation image which is displayed on the display screen of an image display unit, along with the radiation image.

2. Description of the Related Art

A computed radiographic (CR) system has recently been put to practical use to obtain radiation images ranging over a very wide radiation exposing area. In this CR system, the radiation-image information of a subject such as a human body is temporarily recorded on an accumulative fluorescent sheet. The accumulative fluorescent sheet accumulates part of the energy of radiation (X-rays, $\alpha$-rays, $\beta$-rays, $\gamma$-rays, electron rays, ultraviolet rays, etc.) if the radiation is emitted, and emits accelerated fluorescent light in accordance with the accumulated energy if excitation light such as visible light is emitting, thereafter. The sheet with the image information recorded thereon is scanned by excitation light such as a laser light beam and is caused to emit accelerated fluorescent light corresponding to the image information which is signal light. The emitted fluorescent light is read by photoelectric reading means such as a photomultiplier, whereby an image signal is obtained. Based on this image signal, the radiation image of the subject is output as the visible image to a storage medium such as photosensitive material and to a display unit such as a cathode-ray tube (CRT) display unit (Japanese Unexamined Patent Publication Nos. 55(1980)-12429, 56(1981)-11395, and 56(1981)-11397).

For the accumulative fluorescent sheet that is employed in the CR system, half size, large-square size, quarter size, one-sixth size, etc., have been prepared according to the photographic object. Also, in order to record a lengthy subject as a single image, investigation has recently been carried out with respect to performing photographing and recording by employing two or more sheets of the existing sizes, such as half size, put side by side, or by employing a sheet longer than the existing sizes.

Incidentally, in orthopedic surgery and the like, among medical fields, the negative film from which a radiation image was output is employed not only for observation and photographing but also for the purposes of measuring scoliotic curvature (Cobb method and Ferguson method) and a kyphotic index. Measuring points are actually marked on the film from which a radiation image was output, and the distance, angle and the like between the marked measuring points are manually measured with a measuring tool such as a ruler, a protractor and the like. Based on the measured distance and the like, the aforementioned scoliotic curvature and the like are obtained by calculations.

Since, on the other hand, the radiation image obtained by the CR system is digital data as described above, measurements can be made automatically, by displaying the radiation image on the display screen of an image display unit, then specifying measuring points on this display screen, and storing a method of measurement in advance. Furthermore, if methods of calculation for the aforementioned scoliotic curvature and the like are stored, it will become possible to calculate these automatically and the measuring load of a measurer, such as a doctor, a radiation technician and the like, can be reduced appreciably.

In the above-mentioned orthopedic surgery and the like, incidentally, the same subject is again measured by photographing a radiation image in order to judge the course of the medical treatment, and the result of measurement is often compared with the previous result of measurement.

When making measurements on film, as described above, points on the present film corresponding to the pervious marked points are marked and measured, while the present film is being compared with the previous film on which the previous measurement was made.

However, when measurements are made based on the radiation image displayed on the display screen of the image display unit, as described above, it cannot accurately be grasped which point on the radiation image displayed on the display screen has been measured and what measurement result has been obtained. Particularly, when a doctor or a radiation technician making the present measurement differs from a doctor or the like who made the previous measurement, it is difficult to recognize the previous measuring points and measurement result and there is a problem that an accurate comparison between measurement results cannot be performed.

SUMMARY OF THE INVENTION

The present invention has been made in view of the aforementioned circumstances. Accordingly, the object of the present invention is to provide a radiation-image storing method and a radiation-image storing unit which render it easy to recognize the positional information and the like of measuring points afterwards, with respect to a radiation image including measuring points which are predetermined measuring objects, displayed on the display screen of an image display unit.

In accordance with one aspect of the present invention, there is provided a storing method comprising the step of:

storing a radiation image displayed on a display screen of an image display unit, the radiation image including a measuring point which is a measuring object; and wherein positional information of the measuring point specified on the display screen is stored in a storage medium along with the radiation image.

In a preferred form of the storing method, a result of measurement, obtained based on the positional information, is stored along with the radiation image and the positional information.

The positional information of the measuring point and the measurement result may be stored as numerical information (data), along with the radiation image (data). The positional information and the measurement result may also be stored as image information, which is embedded in the radiation image and displayed. In addition, the positional information and the measurement result may be stored as overlay image information, which is overlaid on the radiation image and displayed. Furthermore, numerical information may be embedded in image information so that it does not disturb diagnosis, as in a digital watermark.

The expression "positional information of the measuring point is stored in a storage medium along with the radiation image" means that the positional information and the radiation image are caused to correspond to each other and are stored in a storage medium, and is not always limited only to integrating the positional information and the radiation information and storing in a single storage medium, as described above, but also includes storing the positional information and the radiation image in separate storage media, respectively, as long as both are caused to correspond to each other.

It is preferable that the radiation image, which is stored, be an entire image representing the whole of the radiation image and an enlarged image of a portion of the entire image displayed for specifying the measuring point. The reason for this is that an operator (a doctor, a radiation technician, etc.) is able to recognize the position of a specified measuring point as the approximate position on the entire image and also as the detailed position on the enlarged image.

Note that the enlarged image is obtained by enlarging a portion of the entire image displayed on the display screen, indicated by an indicating mark, and also by overwriting and displaying the enlarged portion on an area including the enlarged portion. Also, the enlarged image may be obtained by enlarging and displaying a portion, indicated in the entire image by an indicating mark, on an area on the display screen differing from an area on which the entire image is displayed. That is, an entire image, which represents the whole of a radiation image including a measuring point that is a measuring object, is displayed on the display screen of an image display unit. In the entire image, a portion of the entire image is indicated by an indicating mark and overwritten to an area including that portion indicated by the indicating mark. Alternatively, the image of a portion of the entire image may be enlarged and displayed on an area on the display screen differing from an area on which the entire image is displayed. The measuring point is specified in the enlarged and displayed image of the aforementioned portion by the indicating mark, whereby detailed positional information of the specified position is acquired. Based on the obtained positional information, the predetermined measurement is carried out, whereby an accurate result of measurement based on an accurate specified position can be obtained.

The expression "enlarge and display a portion of the entire image" does not only mean that a portion of the entire image is enlarged and displayed so that it becomes larger than the portion in the entire image. That is, it will be sufficient if the enlarged and displayed portion is larger than the corresponding portion in the entire image as a result of enlargement. That is, from an accumulative fluorescent sheet, a radiation image is read with high resolution, such as 4280 (vertical)×3520 (horizontal) pixels for half size, 8650 (vertical)×3520 (horizontal) pixels for two half sizes put side by side, and 12840 (vertical)×3520 (horizontal) pixels for three half sizes. However, in an image display unit with resolution which is employed as an ordinary terminal, only a portion of an obtained radiation image can be displayed and therefore there are cases where the number of pixels of the obtained radiation image is reduced to grasp the positional relation of a measuring point, which is a measuring object, to the entire radiation image and the reduced entire radiation image is displayed. As enlargement display of a portion of the entire image in such a case, a portion of the original radiation image may be displayed at its original size or may be enlarged and displayed, instead of reducing the original radiation image and then enlarging a portion of the reduced entire image.

While an approximate position of a measuring point is being recognized on the displayed entire image whose number of pixels was reduced in this manner, the measuring point can be specified accurately on the image of the enlarged and displayed portion.

The phrase "enlarge and display" has the same meaning as enhancing resolution and displaying, as long as resolution is uniform over the entire display screen. That is, the number of pixels constituting a portion of the entire image, enlarged and displayed, means that it is greater than the number of pixels constituting the corresponding portion displayed as the entire image. Therefore, when an enlarging process is actually performed on a portion that is enlarged and displayed, an interpolating process is performed to increase the number of pixels. As this interpolating process, a spline interpolating process, a sharpness adjustable interpolating process (Japanese Unexamined Patent Publication Nos. 9(1997)-50515 and 9(1997)-93426), etc., can be applied in addition to an ordinary linear interpolating process.

For the image of a portion to be enlarged and displayed, it is preferable to perform image processing which differs from that performed on the entire image, in order to make observation of fine portions easy.

The indicating mark may be a cursor of the form that indicates mainly one point on an entire image, like an arrow, a cross mark, etc., or may be, for instance, a magnifying-glass icon that indicates an area of a fixed size. In the case of a cursor of the form that indicates mainly one point, the aforementioned "image of a portion" means the image of an area that includes one point and vicinities.

In displaying the image of a portion of an entire image on a lager scale than the entire image, the image of the enlarged portion may be displayed on an area (a window in a multi-window) differing from a display area for the entire image, or may be overwritten and displayed on an area, indicated by the indicating mark, or its vicinity on the displayed entire image. A form of cutting out a portion of an entire image as a window and enlarging and displaying the image of a portion within this window is included. Note that when a magnifying-glass icon is employed as the indicating mark, the aforementioned portion may be enlarged and displayed within the interior area of the magnifying-glass icon.

Furthermore, an indicating mode and a specifying mode may be switched. In the indicating mode, a measuring-point specifying mark in the image of a portion, enlarged according to a ratio of the above-mentioned enlargement, moves in synchronism with movement of an indicating mark in the entire image. In the specifying mode, the indicating mark in the entire image moves in synchronism with movement of the measuring-point indicating mark in the image of a portion enlarged and displayed. That is, if the indicating mark is moved on the entire image to indicate an approximate position of a measuring point in the entire image, the image of a portion, which is enlarged and displayed, and the measuring-point specifying mark are scrolled in synchronism with movement of the indicating mark by the movement amount of the indicating mark multiplied by the enlargement ratio, within the display area (regardless of whether they are displayed on a portion of the display area for the entire image or a multi-window). Conversely, if the indicating mark is caused to move in synchronism with movement of the measuring-point specifying mark, the positional relation between the measuring-point specifying mark in the image of a portion, enlarged and displayed, and the indicating mark in the entire image can be maintained constant at all times. At the same time, the image of a portion, enlarged and displayed, can be prevented from being scrolled excessively by movement of the indicating mark during the time that the measuring-point specifying mark is moving finely from point to point for specifying a measuring point in the image of a portion enlarged and displayed.

Note that in moving both marks in synchronism with each other, the movement amount of the driven mark is determined based on the enlargement ratio of the above-mentioned enlargement display.

In a preferred form of the present invention, the positional information of the measuring point, thus specified on the enlarged and displayed image by the measuring-point specifying mark, and a result of a predetermined measurement, made based on this positional information, are stored as numerical information, as part of radiation-image information, or as overlay image information which is overlaid on a radiation image and displayed, as described above. In this case, the overlay image information may also be stored in a different storage medium separate from the original radiation-image information.

In accordance with another aspect of the present invention, there is provided a storing unit comprising:

a storage medium for storing a radiation image displayed on a display screen of an image display unit, the radiation image including a measuring point which is a measuring object; and measurement-information storing means for relating positional information of the measuring point specified on the display screen to the radiation image and storing the related positional information in the storage medium along with the radiation image.

In a preferred form of the storing unit, the measurement-information storing means stores a result of measurement, obtained based on the positional information, in the storage medium along with the radiation image and the positional information.

Also, the measurement-information storing means may store the positional information and the measurement result as numerical information. In addition, the measurement-information storing means may store the positional information and the measurement result as image information that is embedded in the radiation image and displayed. Furthermore, the measurement-information storing means may store the positional information and the measurement result as overlay image information that is overlaid on the radiation image and displayed. The operation of "relating positional information of the measuring point specified on the display screen to the radiation image and storing the related positional information in the storage medium along with the radiation image", which is performed by the measurement-information storing means, is not limited to storing the positional information in the same storage medium as the storage medium in which the radiation image is stored, but also includes storing the positional information and the radiation image in separate storage media, as long as both are caused to correspond to each other.

In another preferred form of the storing unit, the radiation image, which is stored, is an entire image representing the whole of the radiation image and an enlarged image of a portion of the entire image displayed for specifying the measuring point. In this case, the enlarged image may be obtained by enlarging a portion of the entire image displayed on the display screen, indicated by an indicating mark, and also by overwriting and displaying the enlarged portion on an area including the enlarged portion. Also, the enlarged image may be obtained by enlarging and displaying a portion, indicated in the entire image by an indicating mark, on an area on the display screen differing from an area on which the entire image is displayed.

The storing method and storing unit according to the present invention stores both a radiation image, displayed on the display screen of an image display unit, and the positional information of a measuring point, specified on the display screen, in a predetermined storage medium.

Therefore, which part of the radiation image has been measured can be recognized accurately and easily, by displaying the stored radiation-image information along with the positional information afterwards. In addition, a result of comparative measurement can be accurately obtained by accurately specifying a corresponding measuring point on another radiation image that is a comparing object.

BRIEF DESCRIPTION OF THE DRAWINGS

The present invention will be described in further detail with reference to the accompanying drawings wherein.

DESCRIPTION OF THE PREFERRED EMBODIMENTS

Figure 1A:
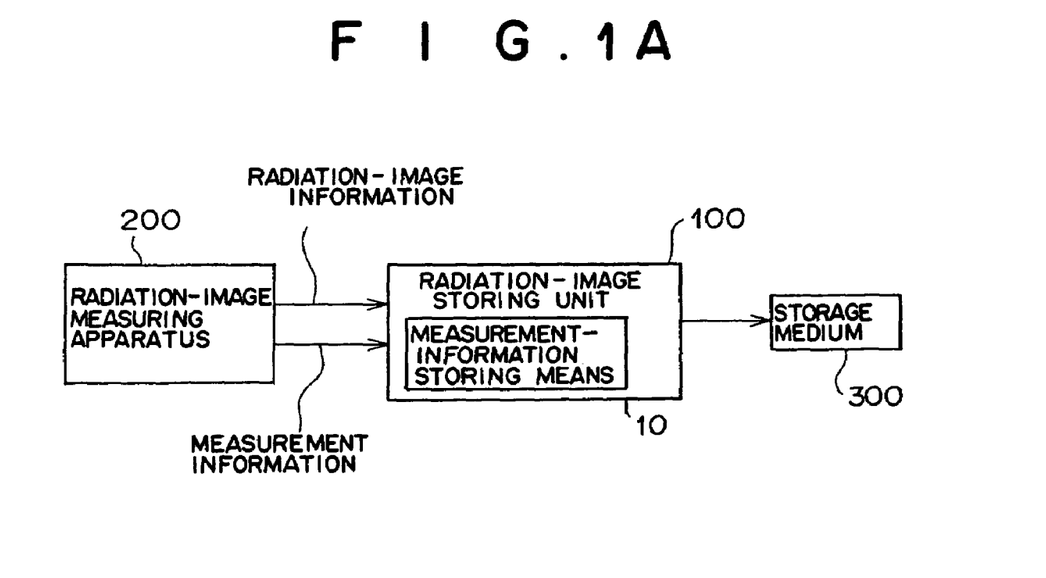
FIG. 1A is a block diagram showing a radiation-image storing unit constructed according to a first embodiment of the present invention.
Figure 1B:
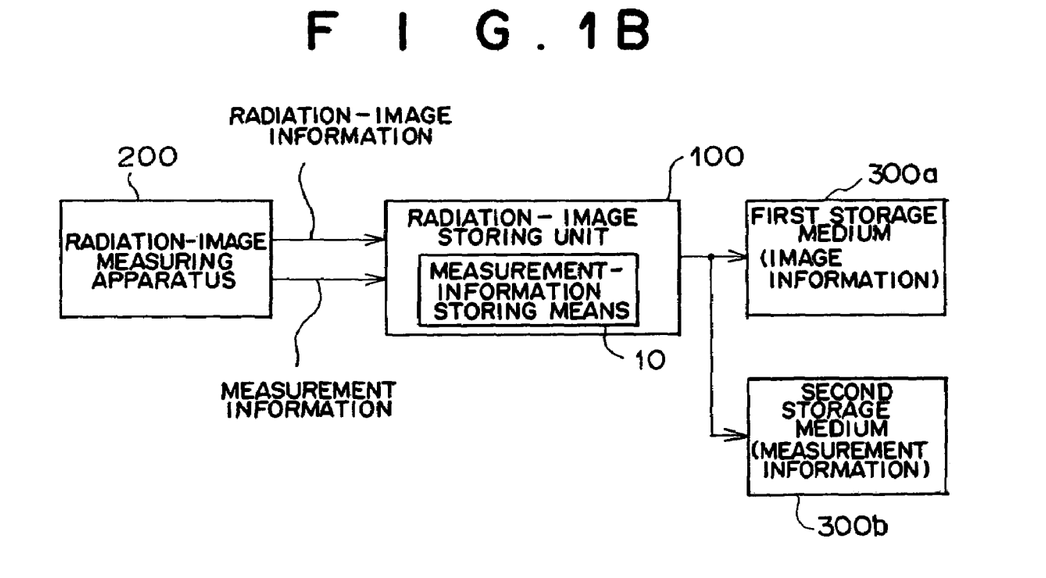
FIG. 1B is a block diagram showing a radiation-image storing unit constructed according to a second embodiment of the present invention.

Referring to FIG. 1, there is shown a preferred embodiment of a radiation-image storing unit in accordance with the present invention. The radiation-image storing unit 100 shown in FIG. 1A includes measurement-information storing means 10. Radiation-image information, which represents a radiation image including a measuring point which is a measuring object, is input from a predetermined radiation-image measuring apparatus 200 to the measurement-information storing means 10. Also, measurement information, which consists of the positional information of a measuring point specified by the radiation-image measuring apparatus 200 and a result of measurement based on the positional information of the specified measuring point, is input from the radiation-image measuring apparatus 200 to the measurement-information storing means 10. The input measurement information is related to the input radiation-image information by the measurement-information storing means 10 and is stored in a predetermined storage medium 300. Note that as shown in FIG. 1B, the radiation-image information may be stored in a first storage medium 300a, while the measurement information related to the radiation-image information may be stored in a second storage medium 300b differing from the first storage medium 300a.

Figure 2:
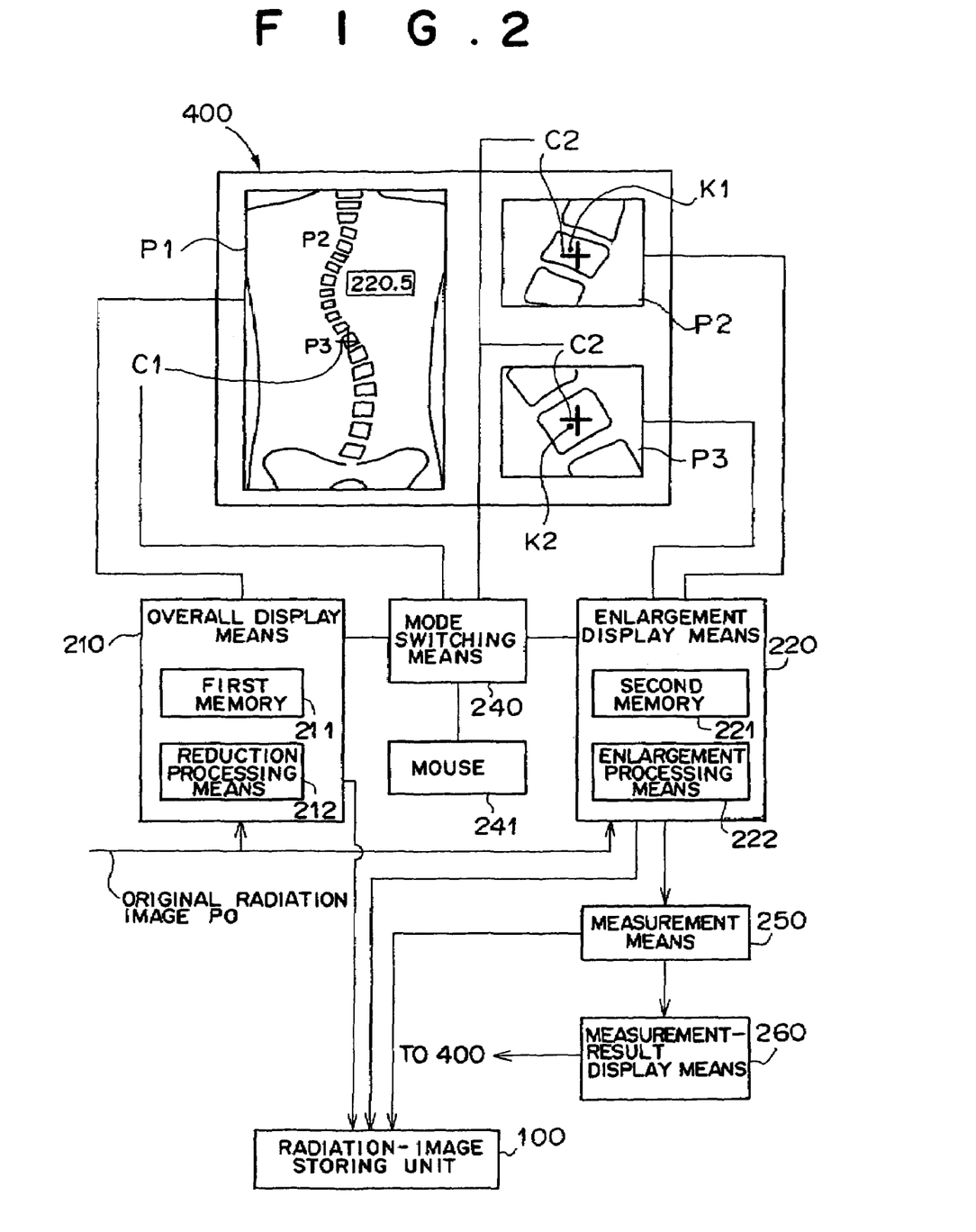
FIG. 2 is a block diagram showing a radiation-image measuring apparatus that inputs a radiation image and measurement information to the radiation-image storing units shown in FIGS. 1A and 1B.

First, the radiation-image measuring apparatus 200 will be described in detail with reference to FIG. 2.

As shown in the figure, the radiation-image measuring apparatus 200 includes overall display means 210. The original radiation image P0 of a human spinal column, including a measuring point which is a predetermined measuring object, is input to the overall display means 210. The overall display means 210 reduces the original radiation image P0 to obtain the entire image P1 of the radiation image and displays the entire image P1 on the left half area of the display screen of an image display unit 400. Also, the radiation-image measuring apparatus 200 includes a first cross cursor C1, enlargement display means 220, and a second cross cursor C2. In the displayed entire image P1, the first cursor C1 is used for indicating a portion of the entire image P1. The original radiation image P0 is also input to the enlargement display means 220. The enlargement display means 220 enlarges the original radiation image P0 and displays images P2 and P3 on the right half of the display screen of the image display unit 400. In the enlarged radiation image, each of the images P2 and P3 corresponds to a portion consisting of a point indicated by the first cross cursor C1 and an area near this indicated point. In the enlarged and displayed images P2 and P3, the second cross cursor C2 is used to specify K1, K2, etc., which are reference points of measurement (measuring points). The radiation-image measuring apparatus 200 further includes measurement means 250, measurement-result display means 260, mode switching means 240, and a mouse 241. The measurement means 250 calculates a result of measurement (e.g., a distance between the measuring points K1 and K2) in accordance with a predetermined algorithm for measurement previously stored, based on the positions of the specified measuring points K1, K2, etc. The measurement-result display means 260 overlays and displays the obtained measurement result on the entire image P displayed on the display screen of the image display unit 400. The mode switching means 240 switches an indicating mode M1 and a specifying mode M2. In the indicating mode M1, the second cursors C2 in the images P2 and P3 of portions, enlarged and displayed in accordance with a ratio of an enlargement ratio obtained by the enlargement display means 220 to a reduction ratio obtained by the overall display means 210 ((enlargement ratio)/(reduction ratio)), move in synchronism with movement of the first cross cursor C1 in the entire image P1. In the specifying mode M2, the first cross cursor C1 in the entire image P1 moves in synchronism with movement of the second cross cursors C2 in the images P2 and P3 enlarged and displayed. The mouse 241 is an interface for arbitrarily moving the cursors C1, C2 within the respective display screens, in accordance with each of the aforementioned modes.

Figure 3:
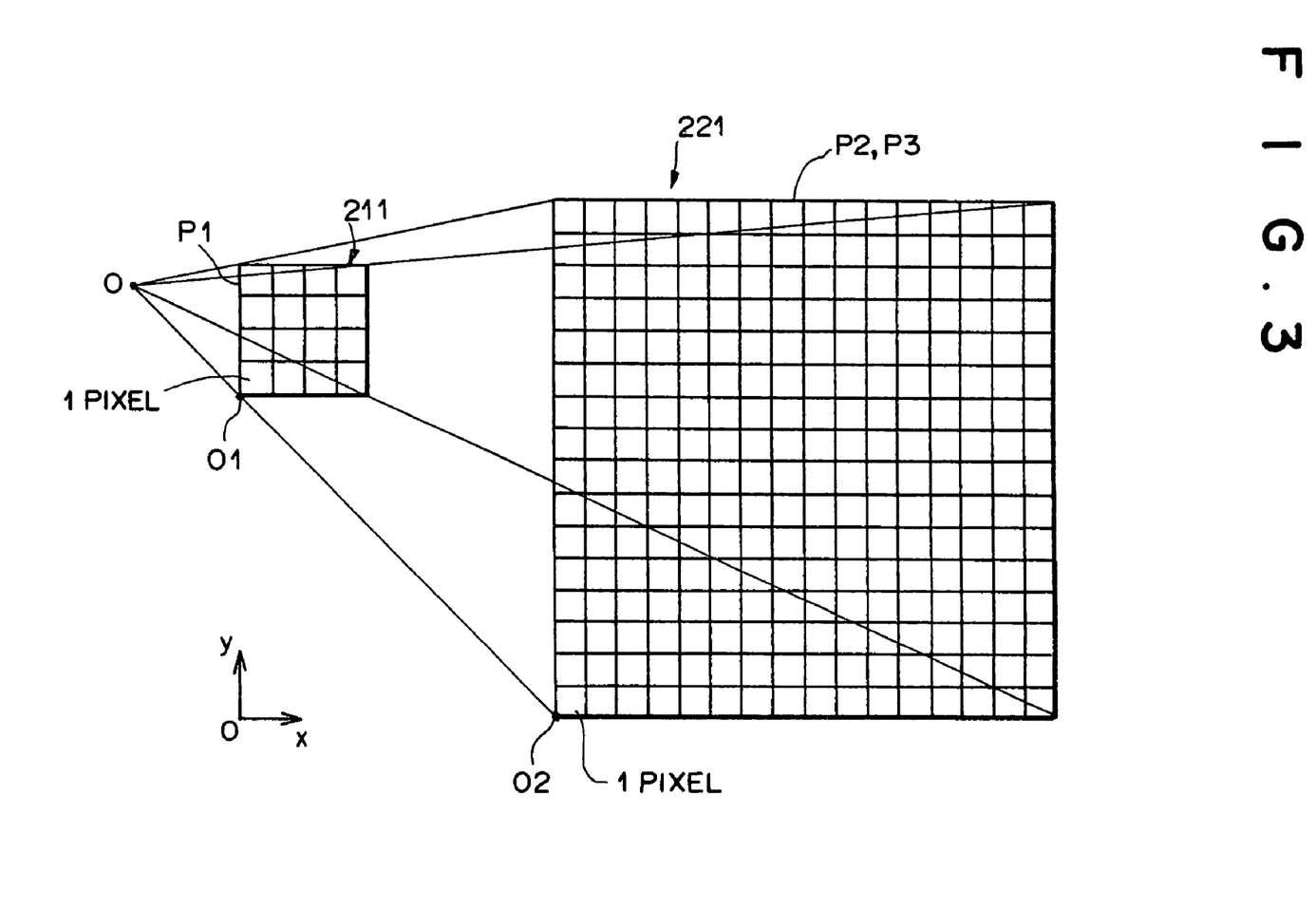
FIG. 3 is a perspective view showing the positional relation between first memory and second memory.

The overall display means 210 is constituted by reduction processing means 212, which reduces the input original radiation image P0, and first memory 211, which stores the entire image P1 obtained by the reduction processing means 212. On the other hand, the enlargement display means 220 is constituted by enlargement processing means 222, which enlarges the input original radiation image P0, and second memory 221, which stores the radiation image obtained by the enlargement processing means 222. The positional relation between the first memory 211 and the second memory 222 has previously been determined according to the value of the above-mentioned ratio ((enlargement ratio)/(reduction ratio)), say, 4), with origins O1, O2 as reference, as shown in FIG. 3. That is, 1 pixel on the first memory 211 is equivalent to 4 pixels on the second memory 221. Therefore, if the first cross cursor C1 is moved by 1 pixel within the entire image P1 on the display screen of the image display unit 400, the enlarged and displayed images P2 and P3 are scrolled by 4 pixels.

The mode switching means 240 is used to selectively switch the indicating mode M1 and the specifying mode M2 by button operation of the mouse 241.

Next, the operation of this radiation-image measuring apparatus 200 will be described in detail.

The original radiation image P0 is input to both the overall display means 210 and the enlargement display means 220. The original radiation image P0 input to the overall display means 210 is reduced by the reduction processing means 212 and stored in the first memory 211. The reduced image P0 is displayed as the reduced entire image P1 on the left half area of the display screen of the image display unit 400. On the other hand, the original radiation image P0 input to the enlargement display means 220 is enlarged by the enlargement processing means 222 and stored in the second memory 221.

At first the mode switching means 240 has already been switched to the indicating mode M1 in which the second cross cursor C2 moves in synchronism with movement of the first cross cursor C1 in the entire image P1. The enlargement display means 220 calculates a point on the enlarged radiation image stored in the second memory 221 which corresponds to the point on the entire image P1 indicated by the first cross cursor C1, and then displays an area near the calculated point on the upper right ¼ area of the display screen of the image display unit 400 as the image P2 of a portion enlarged to a size 4 times the original. When the enlarged image P2 is displayed, the second cross cursor C2 is fixedly displayed at the center of the enlarged image P2.

If the operator manipulates the mouse 241 to move the first cross cursor C1 on the entire image P1, the enlarged image P2 is scrolled within the display screen for the enlarged image P2 by an amount 4 times the movement amount of the first cross cursor C1, in synchronism with the movement of the first cross cursor C1. If the operator indicates the vicinity of the measuring point K1 on the entire image P1 with the first cross cursor C1 by the mouse 241, the enlarged image P2 including the measuring point K1 is displayed on the upper right ¼ enlarged-image display area of the display screen. At this stage, the operator performs the operation of switching the indicating mode M1 to the measuring-point specifying mode M2, with respect to the mode switching means 240 by manipulating the mouse 241. This operation releases the fixation on the second cross cursor C2 in the enlarged image P2, and the operator manipulates the mouse 241 to move the second cross cursor C2 so that the second cross cursor C2 is overlaid on the measuring point K1 on the enlarged and displayed image P2. When the second cross cursor C2 moves, the first cross cursor C1 moves slightly on the entire image P1 in synchronism with the movement of the second cross cursor C2 within the enlarged and displayed image P2.

Since the enlarged and displayed image P2 is displayed with resolution 4 times that of the entire image P1, the operator is able to accurately align the second cross cursor C2 with the measuring point K1, on the enlarged and displayed image P2. After alignment, the operator inputs an instruction to determine a specified measuring point to the enlargement display means 220, manipulating the mouse 241.

In response to the instruction to determine a specified measuring point, the enlargement display means 220 inputs the position of the second cross cursor C2 on the enlarged image P2 to the measurement means 250 and fixes the display of the enlarged and displayed image P2.

Subsequently, in order to specify the other measuring point K2, the operator switches the mode switching means 240 to the indicating mode M1 and again moves the first cross cursor C1 on the entire image P1, by manipulating the mouse 241. The enlargement display means 220 calculates a point on the enlarged radiation image stored in the second memory 221 which corresponds to the point on the entire image P1 indicated by the first cross cursor C1, and then displays an area near the calculated point on the lower right ¼ area of the display screen of the image display unit 400 as the image P3 of a portion enlarged to a size 4 times the original. When the enlarged image P3 is displayed, the second cross cursor C2 is fixedly displayed at the center of the enlarged image P3.

If the operator manipulates the mouse 241 to move the first cross cursor C1 on the entire image P1, the enlarged image P3 is scrolled within the display screen for the enlarged image P3 by an amount 4 times the movement amount of the first cross cursor C1, in synchronism with the movement of the first cross cursor C1. If the operator indicates the vicinity of the measuring point K2 on the entire image P1 with the first cross cursor C1 by the mouse 241, the enlarged image P3 including the measuring point K2 is displayed on the upper right ¼ enlarged-image display area of the display screen. At this stage, the operator performs the operation of switching the indicating mode M1 to the measuring-point specifying mode M2, with respect to the mode switching means 240 by manipulating the mouse 241. This operation releases the fixation on the second cross cursor C2 in the enlarged image P3, and the operator manipulates the mouse 241 to move the second cross cursor C2 so that the second cross cursor C2 is overlaid on the measuring point K2 on the enlarged image P3. When the second cross cursor C2 moves, the first cross cursor C1 moves slightly on the entire image P1 in synchronism with the movement of the second cross cursor C2 within the enlarged image P3.

Since the enlarged image P3 is displayed with resolution 4 times that of the entire image P1, the operator is able to accurately align the second cross cursor C2 with the measuring point K2, on the enlarged image P3. After alignment, the operator inputs an instruction to determine a specified measuring point to the enlargement display means 220, manipulating the mouse 241. In response to the instruction to determine a specified measuring point, the enlargement display means 220 inputs the position of the second cross cursor C2 on the enlarged image P3 to the measurement means 250 and fixes the display of the enlarged image P3.

The measurement means 250 to which the two measuring points K1 and K2 were input in this way calculates a result of measurement, such as a distance between K1 and K2, in accordance with the previously stored algorithm for measurement, based on the information on the positions of the measuring points K1, K2 on the enlarged images that were input. This measurement result is input to the measurement-result display means 260, which in turn displays the input measurement result (e.g., a numeral "200.5" displayed in the entire image P1 shown in FIG. 2) on the display screen of the image display unit 400.

Note that when an instruction to determine a specified measuring point is input via the mouse 241 by the operator, characters P2 and P3 representing the enlarged images P2 and P3 are further displayed near the points that the first cross cursor C1 indicates on the entire image P1. In the entire image P1, the characters P2, P3 indicate the approximate positions of the enlarged images P2, P3, displayed respectively on the upper right ¼ area and lower right ¼ area of the display screen of the image display unit 400.

In this manner, the radiation-image measuring apparatus 200 displays both the entire image P1 of the radiation image, which makes it easy to grasp the positional relation between the measuring points K1 and K2, and the enlarged images P2 and P3, which render it possible to accurately specify the measuring points K1 and K2, on the same display screen of the image display unit 400. The radiation-image measuring apparatus 200 also displays the areas, indicated by the first cursor C1 for indicating the approximate positions of the measuring points K1, K2 in the entire image P1, as the enlarged images P2, P3. Therefore, the radiation-image measuring apparatus 200 is capable of accurately specifying the measuring points K1 and K2, grasping the positional relation between the measuring points K1 and K2 accurately. As a result, the radiation-image measuring apparatus 200 is capable of making an accurate measurement, based on the measuring points K1, K2 specified in this way.

With the aforementioned operation, the entire image P1 and the enlarged images P2 and P3 displayed on the display screen of the image display unit 400 are input as the radiation-image information P from the overall display means 210 and enlargement display means 220 of the radiation-image measuring apparatus 200 to the radiation-image storing unit 100 of the preferred embodiment. In addition, both the information on the positions of the measuring points K1, K2 on the enlarged images P2 and P3 (e.g., a mark "." representing the positions of the measuring points K1, K2 and symbols "K1", "K2") and the measurement result (e.g., a numeral "220.5") are input from the measurement means 250 to the radiation-image storing unit 100 as the measurement information.

Figure 4:
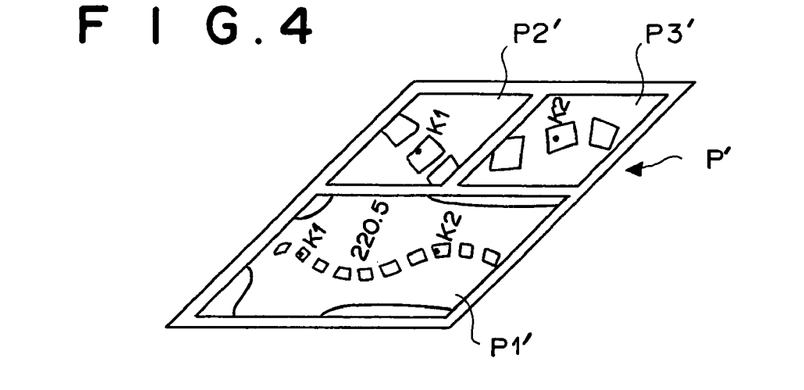
FIG. 4 is a diagram showing radiation-image information embedded with measurement information.

The measurement-information storing means 10 of the radiation-image storing unit 100 causes the input measurement information to correspond to the measured positions of the radiation-image information P and then embeds the measurement information into the radiation-image information P as image information, thereby generating radiation-image information P' (FIG. 4). The generated radiation-image information P' including the measurement information is stored in the storage medium 300 (FIG. 1A).

Thus, in the radiation-image storing unit 100 of the preferred embodiment, the positional information of the measuring points K1, K2 specified on the display screen of the image display unit 400 and the measurement information are stored in the storage medium 300, along with the radiation-image information P displayed on the display screen. Therefore, which part of the radiation image has been measured can be recognized accurately and easily, by displaying the stored radiation-image information P' embedded with the positional information of the measuring points and the measurement result, afterwards. In addition, a result of comparative measurement can be accurately obtained by accurately specifying a corresponding measuring point on another radiation image that is a comparing object. Note that even if the radiation image information P is stored in the first storage medium 300a shown in FIG. 1B and the positional information of K1, K2 and measurement result related to the radiation image information P are stored in the second storage medium 300b shown in the same figure, the same effect can be obtained.

Figure 5:
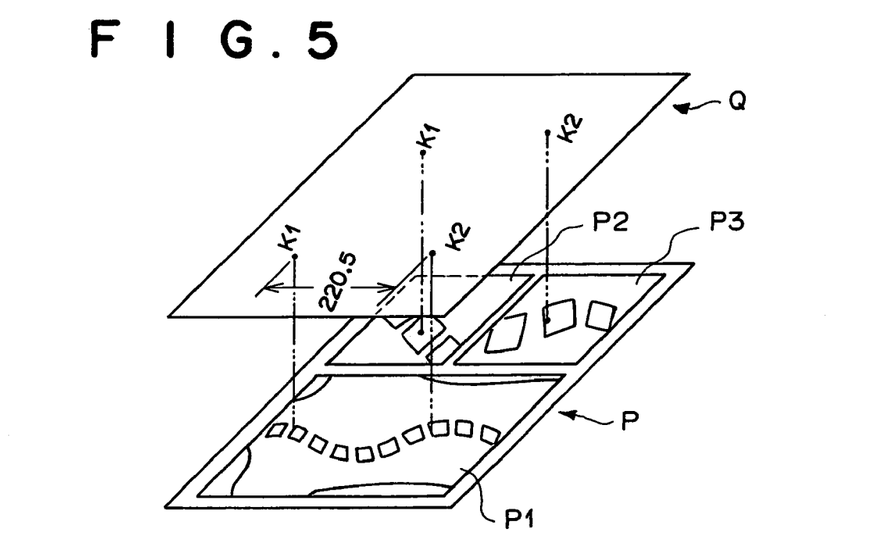
FIG. 5 is an exploded view showing an overlay image in which measurement information is overlaid on radiation-image information, the measurement information and the radiation-image formation being displayed on a multi-window.

Note that in the radiation-image storing unit 100 of the preferred embodiment, although the measurement-information storing means 10 has generated the radiation-image information P' by causing the input measurement information to correspond to the measured positions of the radiation-image information P and by embedding the measurement information into the radiation-image information P as image information, the radiation-image storing unit 100 of the present invention is not limited to this embodiment. For example, as shown in FIG. 5, the input measurement information may be generated as an overlay image Q, which can be overlaid on the radiation-image information P and displayed, and is caused to correspond in position to the radiation-image information P, and this overlay image Q may be stored in the storage medium 300 in correspondence with the radiation-image information P. If the radiation-image information and the measurement information are thus generated as separate images P and Q, the overlay image Q can be overlaid on the radiation-image information P and displayed, when the radiation image is displayed afterwards. In addition, when it is unnecessary to display the measurement information, it is also possible not to display the overlay image Q selectively. Therefore, this case is excellent from the viewpoint of practical convenience.

Figure 6:
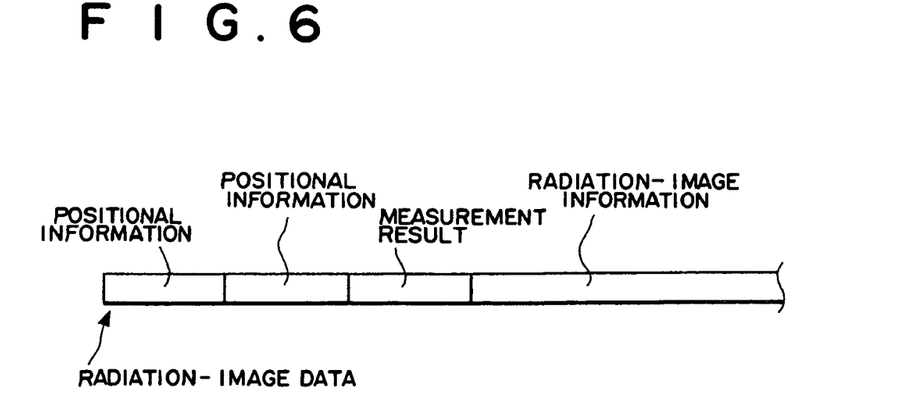
FIG. 6 is a schematic diagram showing an example of a data structure in which measurement information is added to radiation-image information.

In addition, instead of relating the measurement information to the radiation-image information P as image information, the positional information of a measuring point may be expressed, for example, as a coordinate value (x, y) in an x-y coordinate system in FIG. 3 and the measurement result may also be expressed as numerical information. In this case, as shown in FIG. 6, the positional information and the measurement result are added to image data representing the radiation-image information P, to generate radiation-image data, and the generated radiation-image data is stored in the storage medium 300. As with the above case, in displaying the radiation-image information P, it is possible to not display the positional information and the measurement result selectively when it is unnecessary to display the measurement information. Therefore, this case is excellent from the viewpoint of practical convenience.

Figure 7:
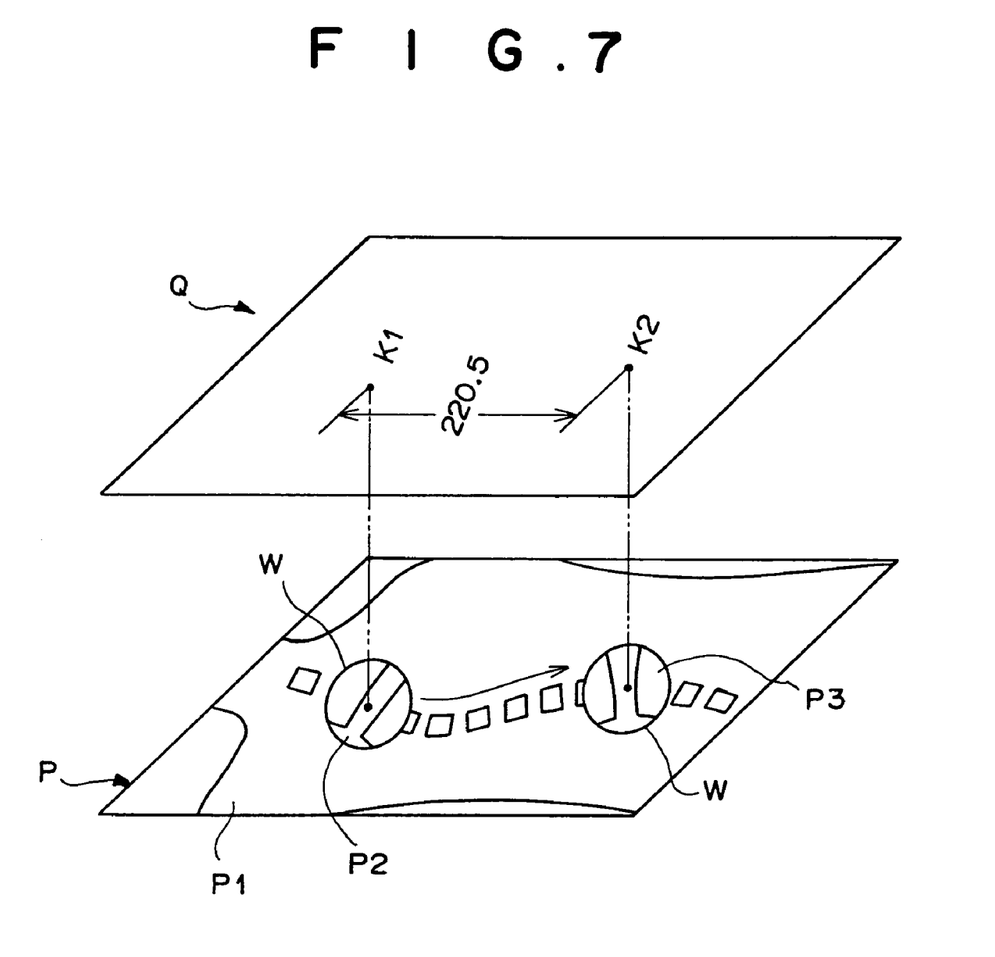
FIG. 7 is an exploded view showing an overlay image in which measurement information is overlaid on radiation-image information, the measurement information and the radiation-image formation being displayed on a single window.

Furthermore, in the radiation-image storing unit of the preferred embodiment, although the entire image P1 and the enlarged image P2 displayed on the different areas of the display screen of the image display unit 400, i.e., images in a multi-window, have been employed as radiation-image information P related to measurement information, the radiation-image storing unit of the present invention is not limited to this embodiment. For instance, as shown in FIG. 7, the measurement information may be stored as an overlay image Q in radiation-image information P, obtained by displaying a movable window W on part of the entire image P and by enlarging the image of a portion of the entire image P displayed within the window W and displaying enlarged images P2, P3.

Figure 8A:
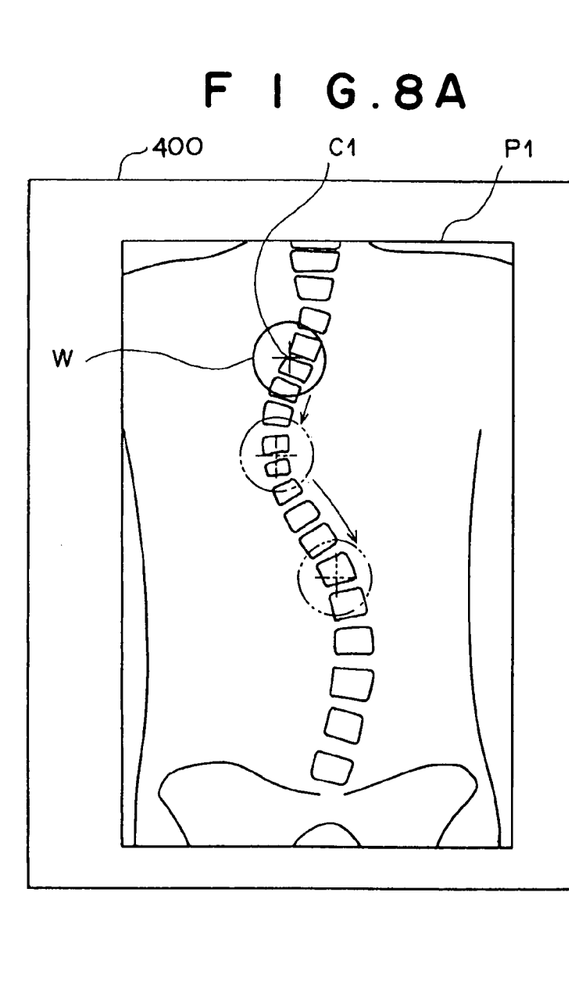
FIGS. 8A and 8B are diagrams used to explain how a measurement is made on a single window by the radiation-image measuring apparatus.
Figure 8B:
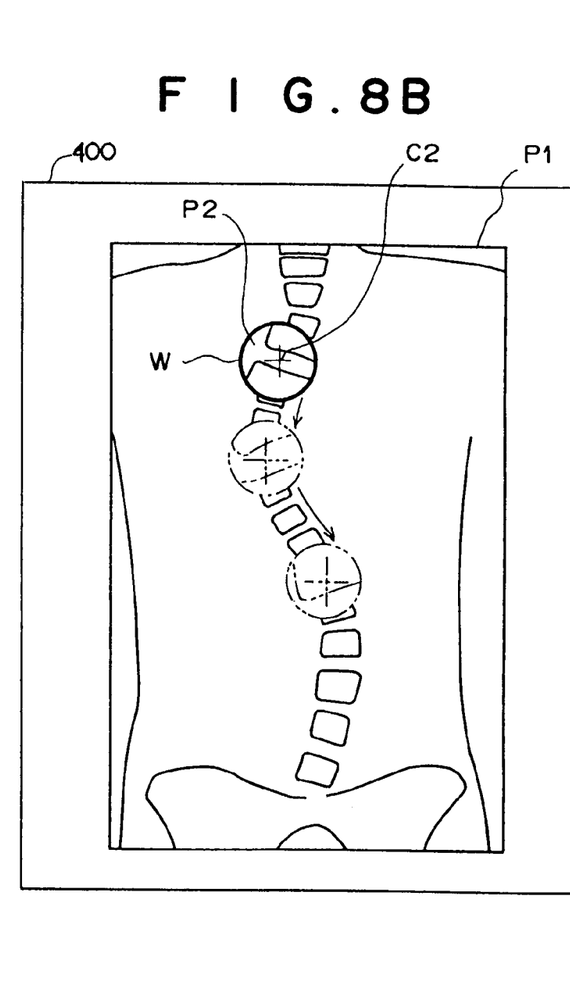

In the radiation-image measuring apparatus in this case, when the mode switching means 240 is in the indicating mode M1, as shown in FIG. 8A, the entire image P1 within a circular area W, as it is, can be displayed in the same way as the outside area, and the first cross cursor C1 and the circular area W can be moved integrally on the entire image P1. When the mode switching means 240 is in the measuring-point specifying mode M2, as shown in FIG. 8B, the first cross cursor C1 functions as the second cross cursor C2, and within the circular area W, a portion of the enlarged image P2, corresponding to the image of a portion which had been displayed within the circular area W when the indicating mode M1 is switched to the specifying mode M2, is displayed. The second cross cursor C2 may be movable freely within the enlarged image P2 displayed within this circular area W. Also, by moving the cursor C2 on the entire image P1 integrally with the circular area W by the mouse 241, in the case where the cursor C2 is always fixed at the central portion of the circular area W, the enlarged image P2 displayed within the circular area W can be scrolled so that the measuring point K1 or K2 is aligned with the cursor C2. As a result, positional relation on the entire image P can easily be grasped at the circular area W and the stopped position on the entire image P1 of the cursor C2, while the measuring point K1 or K2 on the enlarged image P2 is being specified accurately.

While the radiation-image storing unit 100 of the aforementioned embodiment has been constructed separately from the radiation-image measuring apparatus 200, it may be formed integrally with the radiation-image measuring apparatus 200. For example, it may be constructed as a radiation-image storing section.

What is claimed is:

1. A storing method comprising the step of:
    storing a radiation image displayed on a display screen of an image display unit, the radiation image including a measuring point designated for measuring geometric features of an object included in a radiation image; and
    wherein positional information of said measuring point specified on said display screen is stored in a storage medium along with said radiation image, wherein said positional information and a measurement result of said measuring point are stored as image information that is embedded in said radiation image and displayed, wherein said radiation image is an entire image representing the whole of said radiation image and an enlarged image of a portion of said entire image displayed for specifying said measuring point, wherein the measuring point is specified by a user input; and
    displaying a first cursor on the entire image and a second cursor on the enlarged image, and wherein movement of the first and second cursor by the user input are made in conjunction with each other.

2. The storing method as set forth in claim 1, wherein a result of measurement, obtained based on said positional information, is stored along with said radiation image and said positional information.

3. The storing method as set forth in claim 2, wherein said positional information and said measurement result are stored as numerical information.

4. The storing method as set forth in claim 3, wherein said radiation image is an entire image representing the whole of said radiation image and an enlarged image of a portion of said entire image displayed for specifying said measuring point.

5. The storing method as set forth in claim 2, wherein said positional information and said measurement result are stored as image information that is embedded in said radiation image and displayed.

6. The storing method as set forth in claim 2, wherein said positional information and said measurement result are stored as overlay image information that is overlaid on said radiation image and displayed.

7. The storing method as set forth in claim 2, wherein said radiation image is an entire image representing the whole of said radiation image and an enlarged image of a portion of said entire image displayed for specifying said measuring point.

8. The storing method as set forth in claim 1, wherein said positional information and a measurement result of said measuring point are stored as numerical information.

9. The storing method as set forth in claim 8, wherein said radiation image is an entire image representing the whole of said radiation image and an enlarged image of a portion of said entire image displayed for specifying said measuring point.

10. The storing method as set forth in claim 1, wherein said positional information and a measurement result of said measuring point are stored as overlay image information that is overlaid on said radiation image and displayed.

11. The storing method as set forth in claim 1, wherein said radiation image is an entire image representing the whole of said radiation image and an enlarged image of a portion of said entire image displayed for specifying said measuring point.

12. The storing method as set forth in claim 11, wherein said enlarged image is obtained by enlarging a portion of said entire image displayed on said display screen, indicated by an indicating mark, and also by overwriting and displaying the enlarged portion on an area including said portion.

13. The storing method as set forth in claim 11, wherein said enlarged image is obtained by enlarging and displaying a portion, indicated in said entire image by an indicating mark, on an area on the display screen differing from an area on which said entire image is displayed.

14. The storing method of claim 1, wherein movement of the second cursor corresponding to one display pixel corresponds to movement of the first cursor of less than one display pixel, such that movement of the second cursor corresponds to a relatively smaller movement of the first cursor and movement of the first cursor corresponds to a relatively larger movement of the second cursor.

15. The storing method of claim 1 wherein the geometric features include at least one of distance and angle information of the measuring point in relation to a second measurement point of the object of the radiation image.

16. The storing method of claim 1, positional information of said measuring point is stored related to the radiation image.

17. The storing method of claim 1, wherein the geometric features include distance information of the measuring point in relation to a second measurement point of the object of the radiation image.

18. A storing unit comprising:
a storage medium for storing a radiation image displayed on a display screen of an image display unit, the radiation image including a measuring point designated for measuring geometric features of an object included in a radiation image; and
measurement-information storing means for relating positional information of said measuring point specified on said display screen to said radiation image and storing the related positional information in said storage medium along with said radiation image, wherein said positional information and a measurement result of said measuring point are stored as image information that is embedded in said radiation image and displayed, wherein said radiation image is an entire image representing the whole of said radiation image and an enlarged image of a portion of said entire image displayed for specifying said measuring point, wherein the measuring point is specified by a user input; and
wherein the display screen displays a first cursor on the entire image and a second cursor on the enlarged image, and wherein movement of the first and second cursor by the user input are made in conjunction with each other.

19. The storing unit as set forth in claim 18, wherein said measurement-information storing means stores a result of measurement, obtained based on said positional information, in said storage medium along with said radiation image and said positional information.

20. The storing unit as set forth in claim 19, wherein said measurement-information storing means stores said positional information and said measurement result as numerical information.

21. The storing unit as set forth in claim 19, wherein said measurement-information storing means stores said positional information and said measurement result as overlay image information that is overlaid on said radiation image and displayed.

22. The storing unit as set forth in claim 18, wherein said measurement-information storing means stores said positional information and a measurement result of said measuring point as numerical information.

23. The storing unit as set forth in claim 18, wherein said measurement-information storing means stores said positional information and a measurement result of said object as overlay image information that is overlaid on said radiation image and displayed.

24. The storing unit as set forth in claim 18, wherein said radiation image is an entire image representing the whole of said radiation image and an enlarged image of a portion of said entire image displayed for specifying said measuring point.

25. The storing unit as set forth in claim 24, wherein said enlarged image is obtained by enlarging a portion of said entire image displayed on said display screen, indicated by an indicating mark, and also by overwriting and displaying the enlarged portion on an area including said portion.

26. The storing unit as set forth in claim 24, wherein said enlarged image is obtained by enlarging and displaying a portion, indicated in said entire image by an indicating mark, on an area on the display screen differing from an area on which said entire image is displayed.

27. The storing unit of claim 18, wherein the geometric features include at least one of distance and angle information of the measuring point in relation to a second measurement point of the object of the radiation image.

28. The storing unit of claim 27, wherein the geometric features include distance information of the measuring point in relation to a second measurement point of the object of the radiation image.

29. The storing unit of claim 18, wherein the positional information of said measuring point is stored related to the radiation image.

* * * * *